United States Patent [19]

Viner

[11] Patent Number: 5,900,418

[45] Date of Patent: * May 4, 1999

[54] METHOD FOR TREATMENT OF OBESITY

[75] Inventor: Norman Viner, Ottawa, Canada

[73] Assignee: Synapse Pharmaceuticals International, Inc., Ottawa, Canada

[ * ] Notice: This patent issued on a continued prosecution application filed under 37 CFR 1.53(d), and is subject to the twenty year patent term provisions of 35 U.S.C. 154(a)(2).

[21] Appl. No.: 08/795,247

[22] Filed: Feb. 10, 1997

[51] Int. Cl.$^6$ ........................ A61K 31/415; A61K 39/118
[52] U.S. Cl. .................. 514/280; 514/304; 514/305; 514/318; 514/319; 514/383; 514/408; 514/649; 424/263.1; 424/266
[58] Field of Search ..................... 514/380, 304, 514/305, 318, 319, 383, 408, 649; 424/263.1, 266

[56] References Cited

U.S. PATENT DOCUMENTS

| | | |
|---|---|---|
| 2,816,113 | 12/1957 | Wilson et al. . |
| 2,996,510 | 8/1961 | Green . |
| 3,063,901 | 11/1962 | O'Leary et al. . |
| 3,077,476 | 2/1963 | Hackley, Jr. et al. . |
| 3,852,294 | 12/1974 | Hagedorn . |
| 3,867,539 | 2/1975 | Henkin . |
| 3,928,594 | 12/1975 | Cook . |
| 4,002,760 | 1/1977 | Cook . |
| 4,352,810 | 10/1982 | Benschop et al. . |
| 4,446,138 | 5/1984 | Pack . |
| 4,588,724 | 5/1986 | Greenway, III et al. . |
| 4,675,326 | 6/1987 | Amitai et al. . |
| 4,745,122 | 5/1988 | Lassen . |
| 4,865,837 | 9/1989 | Harris, III et al. . |
| 4,925,856 | 5/1990 | Harris, III et al. . |
| 4,988,710 | 1/1991 | Olney . |
| 5,019,594 | 5/1991 | Wurtman et al. . |
| 5,206,371 | 4/1993 | Powers et al. . |
| 5,300,298 | 4/1994 | LaNoue . |
| 5,403,851 | 4/1995 | D'Orlando et al. . |
| 5,567,714 | 10/1996 | Bruns, Jr. et al. . |
| 5,573,774 | 11/1996 | Keenan . |
| 5,578,613 | 11/1996 | Bryant et al. . |

FOREIGN PATENT DOCUMENTS 2016920  10/1979  United Kingdom .

OTHER PUBLICATIONS

Chemical Abstracts, AN 1977:561557, Adams et al, 1977.
Chemical Abstracts AN 1994:671985, Rose et al, 1994.
Simon et al, "Administration of Obidoxime Tablets to Man", Arch. Toxicol, 36:83–88 (1976).

Primary Examiner—Keith MacMillan

[57] ABSTRACT

A method is provided for the control of obesity comprising administering to a mammal including humans suffering from obesity an acetylcholine esterase reactivator or prodrug derivative thereof optionally in association with an acetylcholine receptor antagonist.

41 Claims, No Drawings

METHOD FOR TREATMENT OF OBESITY

BACKGROUND OF THE PRESENT INVENTION

The present invention is directed to a method for the control and/or treatment of obesity.

It is well understood that obesity is a widespread problem. Obesity is linked to a variety of medical conditions including hypertension, diabetes, cardiovascular disease, etc. obesity is also linked to a variety of psychological maladjustments. By contemporary medical standards an obese person is judged to be overweight by at least 10 percent. At present, only a limited number of treatments are available to treat obesity. Exemplary treatments are disclosed in U.S. Pat. Nos. 3,867,539 (administration of histidine); 4,446,138 (administration of L-Dopa); 4,588,724 (administration of beta adrenergic stimulant or alpha-2 adrenergic inhibitor); 4,745,122 (administration of paroxetine); 5,019,594 (sympathomimetic drug and tyrosine); 5,300,298 (administration of 8-phenylxanthines); 5,403,851 (tryptamine); 5,567,714 (administration of neuropeptide Y); 5,573,774 (nicotinic metabolites); and 5,578,613 (administration of 2-phenyl-3-aroylbenzothiophenes). Amphetamine has also been used as an appetite suppressant.

Unfortunately, none of the above methods of treatment have been very successful. While such treatments may bring short-term relief to the person, long-term success has not been easily achieved. The cessation of tobacco use has frequently contributed to weight gain. Also, comorbid addictions, stress, psychiatric disorders and environmental factors may exacerbate the difficulty encountered by a particular person in alleviating obesity. It is believed, for example, that xenobiotic toxic agents such as pesticides, insecticides, fungicides, oxidants, solvents and other environmental toxins encountered by the person by various means (e.g., via drinking water and/or food impurities, etc.) may contribute to the inability of the person to control obesity.

OBJECTS AND SUMMARY OF THE PRESENT INVENTION

It is accordingly an object of the present invention to provide a method for the control and/or treatment of obesity.

In accordance with the present invention, there is accordingly provided a method for the control and/or treatment of obesity comprising administering to a mammal including humans suffering from obesity an effective amount of an acetylcholine esterase reactivator or prodrug derivative thereof optionally in association with an acetylcholine receptor antagonist.

DETAILED DESCRIPTION OF THE PRESENT INVENTION

The present invention is directed to a method for controlling obesity in mammals including humans.

The present invention involves the administration to a mammal suffering from obesity an effective amount of an acetylcholine esterase reactivator optionally in association with an acetylcholine receptor antagonist in order to control and/or treat obesity.

The acetylcholine esterase reactivators which may be employed in the present invention are well known to those skilled in the art and well-described in the literature. Such reactivators found early use as nerve gas and toxic pesticide poisoning antidotes. Exemplary acetylcholine esterase reactivators include but are not limited to those compounds disclosed in U.S. Pat. Nos. 2,816,113; 2,996,510; 3,063,901; 3,077,476; 3,852,294; 3,928,594; 4,002,760; 4,352,810; 4,675,326; 4,865,837; 4,925,856; 4,988,710; 5,206,371 and U.K. application 2,016,920, each herein incorporated by reference in their entirety.

A preferred class of compounds which may be used as acetylcholine esterase reactivators are oximes, generally defined by the formula $(R^1-CR=NOH)^+ X^-$ where R is hydrogen, $C_{1-5}$ alkyl or $NH_2$ and $X^-$ is a pharmaceutically acceptable anion derived from a salt of an inorganic or organic acid. $R^1$ may take many forms. For example $R^1$ may be $C_{1-5}$ alkyl, aryl (e.g., phenyl), or a 5 or 6-membered heterocyclic moiety having from 1 to 3 nitrogen atoms in the heterocyclic ring.

The oxime may also be bicyclic in nature, as defined by the formula $(R^1-CR=NOH)^+ X^-$ where R is hydrogen, $C_{1-5}$ alkyl or $NH_2$ and $R^1$ is

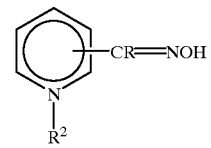

wherein $R^2$ is selected from the group consisting of:

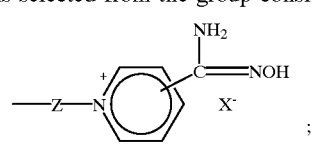

;

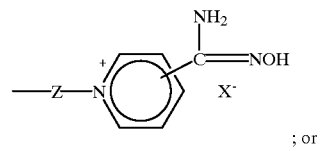

; or

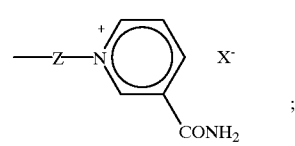

;

where Z is, for example, a polyalkylene group having from 1 to 6 carbon atoms, optionally including at least one ether linkage, such as $-CH_2CH_2-$, $-CH_2OCH_2-$, $-CH_2CH_2OCH_2CH_2-$, $-CH_2OCH_2CH_2OCH_2-$; or $-(CH_2)n$-phenyl-$(CH_2)n$- where n ranges from 1 to 6 and the phenyl moiety may be substituted by $C_{1-5}$ alkyl, and wherein $X^-$ is a pharmaceutically acceptable anion derived from a salt of an inorganic or organic acid. The above formulae are intended to be merely illustrative and not limiting of the identity of the various types of oximes that may be employed in the present invention. Additional oximes not illustrated above exist which possess the ability to reactivate acetylcholine esterase and which may be employed with advantage in the present invention.

Exemplary acetylcholine esterase reactivators include the following oximes: 2-pyridine aldoxime methiodide, 4-pyridine aldoxime methiodide, methyl-2-pyridyl ketoxime methiodide, 1-methyl-pyridinium-2-aldoxime (2-PAM); 2,3-butanedione-2-oxime (DAM), pyruvaldehyde aldoxime (MINA), 2-pyridine aldoxime methochloride (2-PAM-Cl) (marketed as Protopam chloride), pralidoxime methylsulphate (marketed as Contrathion), obidoxime chloride (marketed as Toxogonin), 1,1'-polymethylene bis (4-formylpyridinium) halide oximes; 1,1'-(2,5-dimethyl-p-phenylenedimethylene) bis (4-formylpyridinium) halide dioximes; 1,1'-polymethylene bis (3-formylpyridinium) halide dioximes; 1,1'-(p-phenylenedimethylene) bis (3-formylpyridinium) halide dioximes; bis quaternary 4-formylpyriinium halide monooximes; 1,1'trimethylene bis (3-amidooximopyridinium) halides, quaternary pyridine aldoxime (TMB-4); HI-6; diacetyl monoxime; aldoxime-substituted triazolium compounds including 1,4-dimethyl-3-(hydroxyimino)methyl-1,2,4-triazolium chloride, 1-benzyl-3-(hydroxyimino)methyl-4-methyl-1,2,4-triazolium chloride, and 3-(hydroxyimino)methyl-1-methyl-4-(2'-methylsulfonyl-1'-ethyl)-1,2,4-triazolium chloride; and aldoxime-substituted imidazolium derivatives such as 1-([1'-(2'-butynyloxy)methyl]-2-(hydroxyimino)methyl-3-methylimidazolium chloride, 2-(hydroxyimino)methyl3-methyl-1-[1'-2'-(methylsulfonyl)ethyloxy)methyl)-imidazolium chloride, 2-(hydroxyimino)methyl-3-methyl-1-[(2'-methyl-2'-nitropropyloxy)methyl]-imidazolium chloride, 1-[(2'-N,N-dimethylaminium)- 1'-ethyl]2-(hydroxyimino)methyl-3-methylimidazolium chloride, 1-[2'-(hydroxyimino)methyl-3'-methyl-1'-imidazolo]-3-(4"-carbamoyl-1"-pyridino) propane dichloride, 1-(3'-bromopropyl-1'-oxy)methyl-2-(hydroxyimino)methyl-3-methylimidazolium chloride, 2-(hydroxyimino)methyl-3-methyl-1-(2'-pyrrdidinium-1'-)ethylimidazolium chloride hydrochloride, 1-(3'-butynyl-1'-thio)methyl-2-(hydroxyimino)methyl-3-methylimidazolium chloride, and 1-[(2'-N-ethyl-N-trifluoromethane sulfonyl) amino-1'-]ethyl-2-hydroxyimino)methyl-3-methylimidazolium chloride.

A preferred class of oximes suitable for use in the present invention may be depicted by the formula:

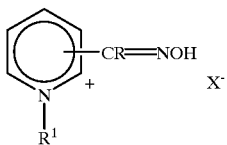

wherein R is hydrogen, $C_{1-5}$ alkyl, or $NH_2$; $R^1$ is $C_{1-5}$ alkyl (particularly methyl or ethyl), and X is an anion portion of the salt $R^1X$. Suitable acid addition salts include the chloride salt, the iodide salt and the methanesulfonate salt.

A specific oxime which is preferred for use in the present invention is 2-PAM chloride which is depicted by the following formula:

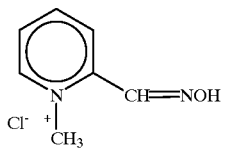

It is also advantageous to administer prodrug derivatives of oximes as disclosed in U.S. Pat. Nos. 3,929,813 and 3,962,447. Such prodrug derivatives exhibit an enhanced ability to pass the blood/brain barrier.

It is believed that oxime-carbamate and oxime carbonate derivatives of oximes as well as hydrazone, semicarbazone and acyl hydrazone derivatives of 2-formyl-1-substituted pyridinium compounds may be usefully employed as acetylcholine esterase reactivators as described in U.S. Pat. Nos. 5,124,455 and 5,206,371, herein incorporated by reference.

The acetylcholine receptor antagonists which may optionally be employed in the present invention are well known to those skilled in the art and well-described in the literature. Exemplary antagonists include but are not limited to (singly or in combination) scopolamine, homatropine, atropine, methscopolamine, methylatropine, ipratropium, methylecgonidine (MEG), mecamylamine, benactyzine, benztropine, trihexyphenidyl, biperiden, procyclidine, benzetimide, dexetimide, iaprophen and pharmaceutically acceptable derivatives thereof. See, for example, U.S. Pat. Nos. 5,011,853 and 5,552,407, herein incorporated by reference in their entirety, which disclose exemplary acetylcholine receptor antagonists. Preferred antagonists are scopolamine and ipratropium.

Acetylcholine esterase reactivators (such as 2-PAM and HI-6) have been used in conjunction with acetylcholine receptor antagonists (such as atropine) to provide in vivo protection against nerve gas agents and other organophosphate poisons. See, for example, U.S. Pat. Nos. 3,063,901; 4,713,391; 4,865,837; and 4,925,856. However, an acetylcholine esterase reactivator (optionally together with an acetylcholine receptor antagonist) has not previously been employed to treat obesity. The amounts of the respective components required to provide the benefits of the present invention are orders of magnitude less than the amounts normally administered to provide protection against nerve gas agents or toxic organophosphate poisoning.

In addition to the acetylcholine esterase reactivator and the acetylcholine receptor antagonist, it is within the scope of the present invention to co-administer additional compounds to assist in achieving the desired result or to provide additional cooperative treatment.

For example, it is advantageous to administer a stimulant in association with the cholinesterase reactivator. A preferred stimulant is nicotine. Nicotine may be administered by any appropriate means, including nicotine gum, a nicotine patch, etc. Nicotine administration may occur prior to, during or subsequent to administration of the two compounds. It has been found that the amount of nicotine administered is less than the amount found in a patch or a stick of nicotine gum (e.g., one milligram or so, the amount not being particularly critical).

Other conventional stimulants (such as dopaminergic stimulants) may be administered in lieu of or in addition to nicotine. Such alternative stimulants include but are not limited to mineptine, Amphetamine, Amphetaminil, Bemegride, Benzphetamine, Brucine, Chorphentermine, Clofenciclan, Clortermine, Cocoa, Demanyl Phosphate, Dexoxadrol, Dextroamphetamine Sulfate (Dexedrine), Diethpropion, N-Ethylamphetamine, Ethamivan, Etifelmin, Etryptamine, Fencamfamine, Fenethylline, Fenosolone, Fenfluramine, Flurothyl, Hexacyclonate Sodium, Homocamfin, Mazindol, Megexamide, Methamphetamine, Methylphenidate, Nicotinic agonists, Nikethamide, Pemoline, Pentylenetetrazole, Phenidimetrazine, Phenmetrazine, Phentermine, Picrotoxin, Pipradrol, Prolintane, Pyrovalerone, and Tetrahydrobenzothienopyridines and mixtures thereof.

Xanthines are an additional class of compounds that may be administered in conjunction with the acetylcholine esterase reactivator and one or more of the other optional active ingredients to assist in signal modulation along the dendrite. U.S. Pat. Nos. 4,364,922; 4,980,379; 5,288,721; 5,340,813; 5,354,756; 5,440,041; 5,473,070; 5,567,704; 5,580,873; and 5,580,874 disclose exemplary xanthines which may be used in the present invention, each herein incorporated by reference. Exemplary xanthines include but are not limited to alkylxanthines such as propylxanthine and methylxanthine. Methylxanthines include 1,3,7-trimethylxanthine (caffeine), 3,7-dimethylxanthine (theobromine), 1,3-dimethylxanthine (theophylline), aminophylline, 1,8-dimethyl-3-(2-methyl-1-butyl)xanthine, 1,3-dimethyl-8-(n-propyl)xanthine, 1,4-(4-hydroxypentyl)-3,7-dimethylxanthine, and 7-(3-phenylpropenyl) theophylline. Exemplary propylxanthines include (E)-4-(1, 2,3,6-tetrahydro-1,3-dimethyl-2,6-dioxo-9H-purin-8-yl) cinnamic acid and (E)-4-(1,2,3,6-tetrahydro-2,6-dioxo-1,3-dipropyl- 9H-purin-8-yl)cinnamic acid. Prodrug forms of xanthines may also be employed as disclosed in U.S. Pat. Nos. 3,935,196 and 4,061,753, herein incorporated by reference. Such forms exhibit enhanced lipid solubility of the compound.

Adenosine antagonists may also be employed in conjunction with one or more of the above. Such compounds reduce the interstitial concentration of adenosine in myocardial tissue. The compounds may either be a competitive inhibitor or a substance that reduces the concentration of adenosine. A variety of compounds may be used as adenosine antagonists including xanthines (such as those discussed above), imidazopyrimidine, pyraxolopyridine, etazolate, pyrazoloquinoline and triazoloquinazoline. Exemplary adenosine antagonists are described in U.S. Pat. Nos. 4,364,922; 4,980, 379; and 5,364,922, each herein incorporated by reference.

As still yet another compound which may be administered in conjunction with one or more of the above is the inhibiting neurotransmitter gamma-aminobutyric acid (GABA) or a precursor thereof such as L-glutamic acid. GABA receptor agonists and other antiepileptics may be employed such as Epival, Baclofen, Sabril, barbiturates, Gabapentin, Lamotrizine and Riluzolo.

It may also be useful to additionally administer an acetylcholine esterase inhibitor such as Phytostigmine, Neostigmine, Demecarium, Pyridostigmine, Velnacrine, Huperzine A, Tacrine, Aricept (Donepezil hydrochloride), Memric, Artane (trihexyphenidyl), Cogentin (benzotropine mesylate), Benedryl (diphenhydramine hydrochloride), Donepezil hydrochloride, etc.

It is also within the scope of the present invention to combine administration of the active ingredients with more conventional therapies such as antioxidant treatment, vitamin treatment, heavy metal antagonists such as chelating agents and bile-acid binding resins. The identity of such compounds is well known to those skilled in the art as described in Goodman & Gilman's *The Pharmacological Basis of Therapeutics,* 9th edition, 1996.

It is within the scope of the present invention to employ both pharmaceutically acceptable analogs as well as tautomers, isomers and salts of the above listed compounds. Analogs differ from the above compounds by means of added alkyl or aryl substituents, added or deleted halogen moieties, presence of differing linkages such as ether linkage, saturation or unsaturation. As to possible salts, the present invention includes within its scope salts of alkali metals, alkaline earth metals, as well as acid addition salts of hydrochloric, hydrobromic, sulfuric, sulfamic, phosphoric, acetic, propionic, succinic, glycollic, stearic, lactic, malic, tartaric, citric, ascorbic, pamoic, maleic, hydroxymaleic, phenylacetic, glutamic, benzoic, salicylic, sulfanilic, fumaric, etc.

The compounds of the present invention may be administered by any pharmaceutically acceptable means and in any pharmaceutically acceptable form. For instance, the compounds may be administered orally in the form of pills, tablets, solutions, syrups, lozenges, etc. in which the compound is the sole or co-ingredient as the active agent. The compounds may also be administered parenterally (e.g., intravenously, intramuscularly or subcutaneously) in association with a pharmaceutically acceptable carrier. Topical administration such as by transdermal patch is also acceptable. The active components may also be administered by inhalers or internasally.

Tablets or pills may contain the active ingredient(s) in admixture with conventional pharmaceutically acceptable excipients (i.e., inert diluents). Such tablets or pills may be uncoated or coated by conventional techniques to delay disintegration and absorption in the gastrointestinal tract. More specifically, such tablets or pills may include an enteric coating to ensure disintegration and absorption in the intestine. Such coatings are generally comprised of a cellulose lower fatty acid phthalate such as cellulose acetate phthalate.

In the event that the acetylcholine receptor antagonist is administered together with the acetylcholine esterase reactivator, it is preferred that the acetylcholine receptor antagonist be administered prior to the administration of the acetylcholine esterase reactivator. Such sequential administration can be accomplished, for example, by administering the respective compounds by separate sequential oral or parenteral administration. Alternatively, the respective components can be sequentially administered in the form of a lozenge, tablet or pill which contains the two components in separate layers which will dissolve or disentegrate in sequence. Such sequential administration is not required, however.

The acetylcholine esterase reactivator (and optionally the acetylcholine receptor antagonist) are employed or administered in an amount effective to inhibit weight gain or induce weight loss by suppression or reduction of appetite.

With the above in mind, the various compounds of the present invention may be administered within a wide range of dosage levels while still enabling the benefits of the present invention to be achieved. For example, the acetylcholine receptor antagonist is generally administered at a dosage level of from about 0.001 to 10 mg. The acetylcholine esterase reactivator is generally administered at a dosage level of from about 1 mg to 10 mg. Such dosage levels are based on a standard adult body weight of 70 kg. Additional components such as stimulants are generally administered in amounts of from about 0.1 to 10 mg. The xanthine component, if administered, will generally be administered in an amount of from 25 to 300 mg. Other components that may be co-administered may be administered in conventional amounts. Such dosage administrations are repeated as required to provide the desired results, with administrations being repeated every 12 to 36 hours depending upon the extent of withdrawal symptoms observed.

The present invention is illustrated by the following examples which are not intended to be limiting of the scope of the invention but merely illustrative of various preferred and specific embodiments.

EXAMPLE 1

A 24 year old female with a 10 year half-pack per day smoking history stated that she continued to smoke partially to control her weight. This person was given 1 mg of nicotine and 0.01 mg of ipratropium followed by 2.5 mg of Protopam by the oral mucosa route of administration in sequence before lunch and dinner on separate days. On both occasions she reported that her appetite was diminished as was her cravings for sweets.

EXAMPLE 2

A 67 year old female moderately obese ex-smoker was given a trial of Protopam 2.5 mg sl. This person had been on low dose valproic acid 125 mg bid and had been using a nicotine patch on a bi-weekly basis for the preceding 2 years. Upon administration of the Protopam she reported a diminished appetite lasting 5 to 7 days. These findings were reproduced on 3 separate occasions over a 6 week period.

From the above description, one of ordinary skill in the art can readily ascertain the essential characteristics of the present invention. Without departing from the scope of the invention, various changes and/or modifications can be made which are still within the scope and range of equivalence of the attached claims.

What is claimed is:

1. A method for treatment and/or control of obesity in a mammal by inhibiting weight gain or inducing weight loss comprising administering to a mammal suffering from obesity an acetylcholine esterase reactivator or prodrug derivative thereof in an amount effective to treat and/or control such obesity.

2. The method of claim 1 wherein an effective amount of an acetylcholine receptor antagonist is administered in conjunction with said acetylcholine esterase reactivator.

3. The method of claim 1 wherein said acetylcholine esterase reactivator is administered in a pharmaceutically acceptable carrier.

4. The method of claim 2 wherein said acetylcholine receptor antagonist is selected from the group consisting of scopolamine, homatropine, atropine, methscopolamine, methylatropine, ipatropium, mecamylamine and mixtures thereof.

5. The method of claim 1 wherein said acetylcholine esterase reactivator is an oxime.

6. The method of claim 5 wherein said acetylcholine esterase reactivator is an oxime salt.

7. The method of claim 6 wherein said salt is an acid addition salt selected from the group consisting of a chloride, iodide and methanesulfonate salt.

8. The method of claim 7 wherein said acetylcholine esterase reactivator is 2-pyridine aldoxime methochloride (2-PAM Cl).

9. The method of claim 1 wherein said acetylcholine esterase reactivator is selected from the group consisting of 1-methyl-pyridinium-2-aldoxime (2-PAM), 2,3-butanedione-2-oxime (DAM), pyruvaldehyde aldoxime (MINA), bis quaternary pyridine aldoxime (TMD-4), prodrug derivatives thereof and pharmaceutically acceptable salts thereof.

10. The method of claim 1 wherein said acetylcholine esterase reactivator is selected from the group consisting of 1-methyl-pyridinium-2-aldoxime (2-PAM), 2,3-butanedione-2-oxime (DAM), pyruvaldehyde aldoxime (MINA), bis quaternary pyridine aldoxime (TMD-4), obidoxime, prodrug derivatives thereof and pharmaceutically acceptable salts thereof.

11. The method of claim 2 wherein said acetylcholine receptor antagonist is selected from the group consisting of scopolamine and ipratropium, and said acetylcholine esterase reactivator is selected from the group consisting of an oxime, a prodrug thereof and a pharmaceutically acceptable salt thereof.

12. The method of claim 11 wherein said acetylcholine receptor antagonist is scopolamine and said acetylcholine esterase reactivator is 2-pyridine aldoxime methochloride (2-PAM Cl) or a pharmaceutically acceptable prodrug thereof.

13. The method of claim 1 wherein said acetylcholine esterase reactivator is defined by the formula $(R^1-CR=NOH)^+X^-$ where R is hydrogen, $C_{1-5}$ alkyl or $NH_2$, $R^1$ is $C_{1-5}$ alkyl and $X^-$ is a pharmaceutically acceptable anion derived from a salt of an inorganic acid or a salt of an organic acid.

14. The method of claim 1 wherein said acetylcholine esterase reactivator is defined by the formula $(R^1-CR=NOH)^+X^-$ where R is hydrogen, $C_{1-5}$ alkyl or $NH_2$, $R^1$ is aryl and $X^-$ is a pharmaceutically acceptable anion derived from a salt of an inorganic acid or a salt of an organic acid.

15. The method of claim 1 wherein said acetylcholine esterase reactivator is defined by the formula $(R^1-CR=NOH)^+X^-$ where R is hydrogen, $C_{1-5}$ alkyl or $NH_2$ and $R^1$ is a 5 or 6 membered heterocyclic moiety having from 1 to 3 nitrogen atoms in the heterocyclic ring and $X^-$ is a pharmaceutically acceptable anion derived from a salt of an inorganic acid or a salt of an organic acid.

16. The method of claim 1 wherein said acetylcholine esterase reactivator is defined by the formula $(R^1-CR=NOH)^+X^-$ where R is hydrogen, $C_{1-5}$ alkyl or $NH_2$ and $R^1$ is

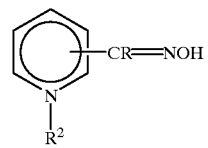

wherein $R^2$ is selected from the group consisting of:

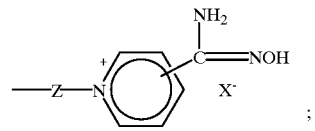

;

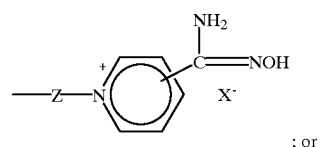

; or

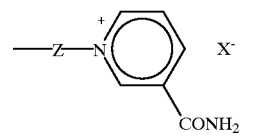

;

where Z is a polyalkylene group having from 1 to 6 carbon atoms, optionally including at least one ether linkage, or —(CH$_2$)n-phenyl-(CH$_2$)n- where n ranges from 1 to 6 and the phenyl moiety may be optionally substituted by $C_{1-5}$ alkyl, and wherein $X^-$ is a pharmaceutically acceptable anion derived from a salt of an inorganic acid or a salt of an organic acid.

17. The method of claim 1 wherein said mammal is a human and said acetylcholine esterase reactivator is administered in an amount within the range of from about 1 to 10 mg per 70 kg body weight.

18. The method of claim 2 wherein said mammal is a human and said acetylcholine receptor antagonist is administered in an amount within the range of from about 0.001 to 10 mg, per 70 kg body weight.

19. The method of claim 2 wherein said acetylcholine esterase reactivator is an oxime.

20. The method of claim 2 wherein said acetylcholine esterase reactivator is an oxime salt.

21. The method of claim 20 wherein said salt is an acid addition salt selected from the group consisting of a chloride, iodide, and methanesulfonate salt.

22. The method of claim 20 wherein said acetylcholine esterase reactivator is selected from the group consisting of 2-pyridine aldoxime methochloride (2-PAM Cl) and obidoxime chloride.

23. The method of claim 2 wherein said acetylcholine esterase reactivator is selected from the group consisting of 1-methyl-pyridinium-2-aldoxime (2-PAM), 2,3-butanedione-2-oxime (DAM), pyruvaldehyde aldoxime (MINA), bis quaternary pyridine aldoxime (TMD-4), obidoxime, prodrug derivatives thereof and pharmaceutically acceptable salts thereof.

24. The method of claim 2 wherein said acetylcholine esterase reactivator is defined by the formula $(R^1—CR=NOH)^+X^-$ where R is hydrogen, $C_{1-5}$ alkyl or $NH_2$, $R^1$ is $C_{1-5}$ alkyl and $X^-$ is a pharmaceutically acceptable anion derived from a salt of an inorganic acid or a salt of an organic acid.

25. The method of claim 2 wherein said acetylcholine esterase reactivator is defined by the formula $(R^1—CR=NOH)^+X^-$ where R is hydrogen, $C_{1-5}$ alkyl or $NH_2$, $R^1$ is aryl and $X^-$ is a pharmaceutically acceptable anion derived from a salt of an inorganic acid or salt of an inorganic acid.

26. The method of claim 2 wherein said acetylcholine esterase reactivator is defined by the formula $(R^1—CR=NOH)^+X^-$ where R is hydrogen, $C_{1-5}$ alkyl or $NH_2$ and $R^1$ is a 5 or 6 membered heterocyclic moiety having from 1 to 3 nitrogen atoms in the heterocyclic ring and $X^-$ is a pharmaceutically acceptable anion derived from a salt of an inorganic acid or a salt of an organic acid.

27. The method of claim 2 wherein said acetylcholine esterase reactivator is defined defined by the formula $(R^1—CR=NOH)^+X^-$ where R is hydrogen, $C_{1-5}$ alkyl or $NH_2$ and $R^1$ is

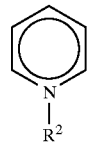

where $R^2$ is selected from the group consisting of:

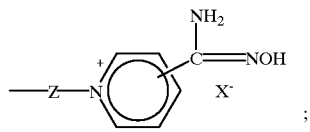

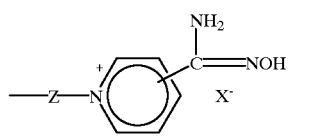

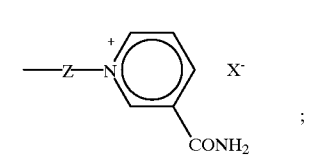

where Z is a polyalkylene group having from 1 to 6 carbon atoms, optionally including at least one ether linkage, or —(CH2)$_n$-phenyl-(CH2)$_n$— where n ranges from 1 to 6 and the phenyl moiety may be optionally substituted by $C_{1-5}$ alkyl, and wherein $X^-$ is a pharmaceutically acceptable anion derived from a salt of an inorganic acid or a salt of an organic acid.

28. The method of claim 2 wherein said acetylcholine esterase reactivator is administered in an amount within the range of from about 1 to 10 mg per 70 kg body weight.

29. A method for treatment and/or control of obesity in a mammal by inhibiting weight gain or inducing weight loss comprising administering to a mammal suffering from obesity an active agent comprising a pharmaceutically acceptable obesity treating or controlling oxime or salt thereof in an amount effective to treat and/or control such obesity.

30. The method of claim 29 wherein an effective amount of an acetylcholine receptor antagonist is administered in conjunction with said active agent.

31. The method of claim 30 wherein said acetylcholine receptor antagonist is selected from the group consisting of scopolamine, homatropine, atropine, methscopolamine, methylatropine, ipatropium, mecamylamine and mixtures thereof.

32. The method of claim 29 wherein said active agent is an oxime salt.

33. The method of claim 32 wherein said salt is an acid addition salt selected from the group consisting of a chloride, iodide and methanesulfonate salt.

34. The method of claim 32 wherein said oxime salt is selected from the group consisting of 2-pyridine aldoxime methochloride (2-PAM Cl) and obidoxime chloride.

35. The method of claim 29 wherein said active agent is selected from the group consisting of 1-methyl-pyridinium-2-aldoxime (2-PAM), 2,3-butanedione-2-oxime (DAM), pyruvaldehyde aldoxime (MINA), bis quaternary pyridine aldoxime (TMD-4), obidoxime, and pharmaceutically acceptable salts thereof.

36. The method of claim 30 wherein said acetylcholine receptor antagonist is selected from the group consisting of scopolamine and ipratropium.

37. The method of claim 29 wherein said active agent is defined by the formula $(R^1—CR=NOH)^+$ $X^-$ where R is hydrogen, $C_{1-5}$ alkyl or $NH_2$, $R^1$ is $C_{1-5}$ alkyl and $X^-$ is a pharmaceutically acceptable anion derived from a salt of an inorganic acid or a salt of an organic acid.

38. The method of claim 29 wherein said active agent is defined by the formula $(R^1—CR=NOH)^+X^-$ where R is hydrogen, $C_{1-5}$ alkyl or $NH_2$, $R^1$ is aryl and $X^-$ is a pharmaceutically acceptable anion derived from a salt of an inorganic acid or a salt of an organic acid.

39. The method of claim 29 wherein said active agent is defined by the formula $(R^1—CR=NOH)^+X^-$ where R is hydrogen, $C_{1-5}$ alkyl or $NH_2$ and $R^1$ is a 5 or 6 membered heterocyclic moiety having from 1 to 3 nitrogen atoms in the heterocyclic ring and $X^-$ is a pharmaceutically acceptable anion derived from a salt of an inorganic acid or a salt of an organic acid.

40. The method of claim 29 wherein said active agent is defined by the formula $(R^1—CR=NOH)^+X^-$ where R is hydrogen, $C_{1-5}$ alkyl or $NH_2$ and $R^1$ is

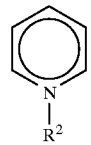

wherein $R^2$ is selected from the group consisting of:

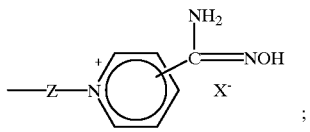

-continued

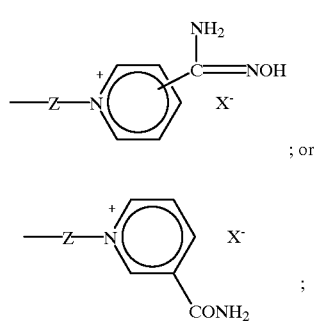

where Z is a polyalkylene group having from 1 to 6 carbon atoms, optionally including at least one ether linkage, or —(CH$_2$)n-phenyl-(CH$_2$)n- where n ranges from 1 to 6 and the phenyl moiety may be optionally substituted by C$_{1-5}$ alkyl, and wherein X$^-$ is a pharmaceutically acceptable anion derived from a salt of an inorganic acid or a salt of an organic acid.

41. The method of claim 29 wherein said active agent is administered in an amount within the range of from about 1 to 10 mg per 70 kg body weight.

* * * * *